(12) United States Patent
Hasegawa et al.

(10) Patent No.: US 11,771,806 B2
(45) Date of Patent: *Oct. 3, 2023

(54) CHAMBER FOR TRANSPLANTATION AND DEVICE FOR TRANSPLANTATION

(71) Applicant: FUJIFILM Corporation, Tokyo (JP)

(72) Inventors: Kazuhiro Hasegawa, Ashigarakami-gun (JP); Ryuta Takegami, Ashigarakami-gun (JP); Kuniyuki Kaminaga, Ashigarakami-gun (JP); Yusuke Mochizuki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 838 days.

This patent is subject to a terminal disclaimer.

(21) Appl. No.: 16/727,817

(22) Filed: Dec. 26, 2019

(65) Prior Publication Data
US 2020/0128814 A1    Apr. 30, 2020

Related U.S. Application Data

(63) Continuation of application No. PCT/JP2018/024666, filed on Jun. 28, 2018.

(30) Foreign Application Priority Data

Jun. 29, 2017    (JP) .................................. 2017-127655

(51) Int. Cl.
*A01N 1/02* (2006.01)
*A61L 27/56* (2006.01)
*A61L 27/16* (2006.01)
*A61L 27/54* (2006.01)
*A61L 27/26* (2006.01)

(52) U.S. Cl.
CPC ............ *A61L 27/56* (2013.01); *A01N 1/0231* (2013.01); *A01N 1/0263* (2013.01); *A61L 27/16* (2013.01); *A61L 27/26* (2013.01); *A61L 27/54* (2013.01); *A61L 2300/43* (2013.01)

(58) Field of Classification Search
None
See application file for complete search history.

(56) References Cited

U.S. PATENT DOCUMENTS

| | | | | |
|---|---|---|---|---|
| 5,713,888 | A * | 2/1998 | Neuenfeldt ............. | A61F 2/022 604/890.1 |
| 6,060,640 | A * | 5/2000 | Pauley ..................... | A61F 2/022 623/1.41 |
| 2004/0154978 | A1* | 8/2004 | Sale ........................ | B29C 41/32 210/488 |
| 2010/0150984 | A1 | 6/2010 | Kennedy et al. | |
| 2010/0209468 | A1 | 8/2010 | Kennedy et al. | |
| 2016/0332119 | A1 | 11/2016 | Fissell et al. | |
| 2017/0266626 | A1 | 9/2017 | Kayama et al. | |
| 2017/0348650 | A1* | 12/2017 | Kayama .................. | C07K 1/34 |
| 2019/0262122 | A1 | 8/2019 | Mochizuki et al. | |
| 2019/0262509 | A1 | 8/2019 | Mochizuki et al. | |

FOREIGN PATENT DOCUMENTS

| | | |
|---|---|---|
| CN | 101528166 A | 9/2009 |
| CN | 101686854 A | 3/2010 |
| CN | 104841021 A | 8/2015 |
| CN | 106573203 A | 4/2017 |
| EP | 2 623 187 A1 | 8/2013 |
| JP | 2005-349093 A | 12/2005 |
| WO | WO 92/07525 A1 | 5/1992 |
| WO | WO 2008/134491 A1 | 11/2008 |
| WO | WO 2016/117565 A1 | 7/2016 |
| WO | WO 2018/088451 A1 | 5/2018 |
| WO | WO 2018/088452 A1 | 5/2018 |

OTHER PUBLICATIONS

Chinese Office Action and Search Report for corresponding Chinese Application No. 201880043780.4, dated Jun. 24, 2021, with English translation of the Office Action.
International Preliminary Report on Patentability, dated Jan. 9, 2020 and Written Opinion of the International Searching Authority, dated Oct. 2, 2019, (Forms PCT/IB/326, PCT/IB/373, and PCT/ISA/237) for Application No. PCT/JP2018/024666, with English translation of the Written Opinion.
International Search Report (Form PCT/ISA/210) for International Application No. PCT/JP2018/024666, dated Oct. 2, 2018, with English translation.
Petersen et al., "Improved Diffusion Properties of a New Polysulfone Membrane for the Development of a Bioartificial Pancreas," Transplantation Proceedings, vol. 33, 2001, pp. 1952-1953.
Tatarkiewicz et al., "Reversal of Hyperglycemia in Mice after Subcutaneous Transplantation of Macroencapsulated Islets," Transplantation, vol. 67, Issue 5, Mar. 15, 1999, pp. 665-671 (10 pages).

(Continued)

*Primary Examiner* — Nghi V Nguyen
(74) *Attorney, Agent, or Firm* — Birch, Stewart, Kolasch & Birch, LLP

(57) ABSTRACT

According to the present invention, there are provided a chamber for transplantation, including a membrane for immunoisolation including a porous membrane at at least part of a boundary between an inside and an outside of the chamber for transplantation, in which the porous membrane contains a polymer and has a layered compact portion where a pore diameter is the smallest within the membrane, a pore diameter continuously increases in a thickness direction from the compact portion toward both one surface A and the other surface B of the porous membrane, a porosity in a vicinity of the surface A is 65% or more, an average pore diameter of the surface A is larger than an average pore diameter of the surface B, and the surface B is disposed on the inside of the chamber for transplantation; and a device for transplantation including the chamber for transplantation enclosing a biological constituent therein. In the chamber for transplantation of the present invention, angiogenesis in a recipient is induced and a deterioration in substance permeability is unlikely to occur.

20 Claims, 1 Drawing Sheet

(56) References Cited

OTHER PUBLICATIONS

Barkai et al., "Survival of encapsulated islets: More than a membrane story," World Journal of Transplantation, vol. 6, Issue 1, Mar. 24, 2016, pp. 69-90.
Desai et al., "Advances in islet encapsulation technologies," Nature Reviews Drug Discovery. vol. 16, May 2017, pp. 338-350.
Extended European Search Report for European Application No. 18824045.1, dated Apr. 22, 2020.
Iacovacci et al., "The bioartificial pancreas (BAP): Biological, Chemical and Engineering Challenges," Biochemical Pharmacology, vol. 100, 2016, pp. 12-27.
Nyitray et al., "Polycaprolactone thin-film micro- and nanoporous cell-encapsulation devices." ACS Nano, vol. 9, No. 6, 2015, pp. 5675-5682.
Stamatialis et al., "Medical applications of membranes: drug delivery, artificial organs and tissue engineering," Journal of Membrane Science, vol. 308, 2008, pp. 1-34.

\* cited by examiner

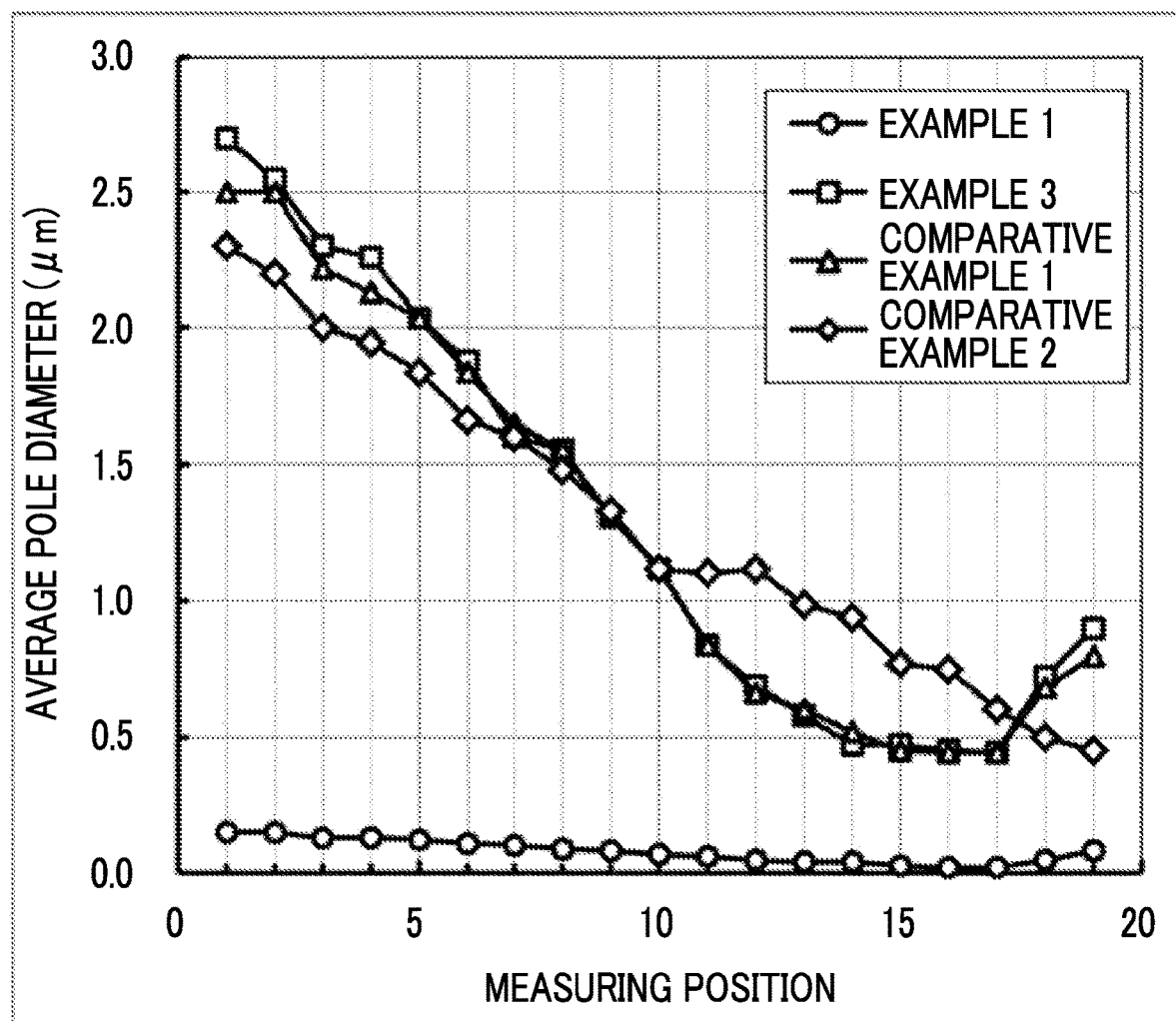

2

CHAMBER FOR TRANSPLANTATION AND DEVICE FOR TRANSPLANTATION

CROSS-REFERENCE TO RELATED APPLICATIONS

This application is a continuation of PCT International Application No. PCT/JP2018/024666 filed on Jun. 28, 2018, which claims priority under 35 U.S.C. § 119 (a) to Japanese Patent Application No. 2017-127655 filed on Jun. 29, 2017, the entire content of which is incorporated herein by reference.

BACKGROUND OF THE INVENTION

1. Field of the Invention

The present invention relates to a chamber for transplantation which includes a membrane for immunoisolation, and a device for transplantation which includes the chamber for transplantation.

2. Description of the Related Art

Immunoisolation is one of methods for preventing immune reactions in a recipient during transplantation of biological constituents such as cells, tissues, or organs. A membrane for immunoisolation is a selectively permeable membrane which allows water, oxygen, glucose, or the like to permeate, and which, at the same time, performs immunoisolation by inhibiting permeation of immune cells and the like involved in an immune rejection. For example, while preventing an immune rejection, it is possible to achieve a purpose of transplantation by a device for transplantation utilizing a membrane for immunoisolation which allows physiologically active substances to permeate therethrough, for transplantation of cells secreting the physiologically active substances.

In order to allow continuous supplying of nutrients to transplanted biological constituents and secretion of physiologically active substances from the transplanted biological constituents, the vascular plexus is preferably formed around a device for transplantation. A case where the vascular plexus is not formed and thus the device for transplantation is encapsulated by fibroblasts, can lead to necrosis of biological constituents. Such a characteristic in formation of the vascular plexus is shown to depend on a microstructure of a membrane for immunoisolation.

Transplantation, 67, 665 (1999) discloses that transplantation is performed using a commercially available chamber for transplantation (TheraCyte (registered trade name)), the chamber being formed by using a porous membrane that is a laminate membrane obtained by laminating a membrane having a pore diameter of 0.45 μm and cell retention properties and an outer membrane of polytetrafluoroethylene (PTFE) having a pore diameter of 5 μm; and that this outer membrane induced the formation of new blood vessels in tissue of a recipient.

SUMMARY OF THE INVENTION

In the chamber for transplantation disclosed in Transplantation, 67, 665 (1999), a surface of the membrane having a smaller pore diameter and cell retention properties in the laminate membrane is on an inner space side. As described above, in a configuration in which a surface of a membrane for immunoisolation has a minimum pore diameter necessary for immunoisolation, a deterioration in substance permeability is likely to occur based on adsorption of proteins or the like.

An object of the present invention is to provide a chamber for transplantation by which angiogenesis in a recipient is induced and in which a deterioration in substance permeability is unlikely to occur, and a device for transplantation.

The inventors of the present invention have conducted intensive studies to achieve the above-mentioned objects, have found a microstructure of a membrane for immunoisolation, in which a deterioration in substance permeability is unlikely to occur, and produced a chamber for transplantation using the microstructure. Thereby, the present invention had been completed.

That is, the present invention provides the following <1> to <11>.

<1> A chamber for transplantation, comprising:
a membrane for immunoisolation at at least part of a boundary between an inside and an outside of the chamber for transplantation,
in which the membrane for immunoisolation includes a porous membrane,
the porous membrane contains a polymer,
the porous membrane has a layered compact portion where a pore diameter is the smallest within the membrane,
a pore diameter continuously increases in a thickness direction from the compact portion toward both one surface A and the other surface B of the porous membrane,
a porosity in a vicinity of the surface A is 65% or more,
an average pore diameter of the surface A is larger than an average pore diameter of the surface B, and
the surface B is disposed on the inside of the chamber for transplantation.

<2> The chamber for transplantation according to <1>, in which an average pore diameter of the compact portion is 0.02 μm to 1.5 μm.

<3> The chamber for transplantation according to <1> or <2>, in which the average pore diameter of the surface A is 1.0 μm to 100 μm.

<4> The chamber for transplantation according to any one of <1> to <3>, in which the average pore diameter of the surface B is 0.1 μm to 10 μm.

<5> The chamber for transplantation according to any one of <1> to <4>, in which the average pore diameter of the surface A is three times or more the average pore diameter of the surface B.

<6> The chamber for transplantation according to any one of <1> to <5>, in which a thickness of the compact portion is 0.5 μm to 30 μm.

<7> The chamber for transplantation according to any one of <1> to <6>, in which a thickness of the porous membrane is 10 μm to 50 μm.

<8> The chamber for transplantation according to any one of <1> to <7>, in which the porous membrane contains polysulfone or polyethersulfone, and at least one kind of hydrophilic polymers.

<9> A device for transplantation, comprising the chamber for transplantation according to any one of <1> to <8> enclosing a biological constituent therein.

<10> The device for transplantation according to <9>, in which the biological constituent releases a physiologically active substance.

<11> The device for transplantation according to <10>, in which the physiologically active substance is insulin.

According to the present invention, it is possible to provide a chamber for transplantation by which angiogenesis in a recipient is induced and in which a deterioration in substance permeability is unlikely to occur. A device for transplantation including the chamber for transplantation of the present invention enclosing a biological constituent therein can be used for a long period of time without occurrence of an immune rejection after transplantation into a recipient.

BRIEF DESCRIPTION OF THE DRAWINGS

FIG. 1 is a view showing pore diameter distribution of porous membranes of Examples 1 and 3 and Comparative Examples 1 and 2.

DESCRIPTION OF THE PREFERRED EMBODIMENTS

Hereinafter, the present invention will be described in detail.

In the present specification, "to" is used to refer to a meaning including numerical values denoted before and after "to" as a lower limit value and an upper limit value.

<<Chamber for Transplantation>>

A chamber for transplantation is a container for transplanting a biological constituent into a recipient. The chamber for transplantation can enclose the biological constituent therein.

The chamber for transplantation according to the embodiment of the present invention has a membrane for immunoisolation in a boundary (a boundary that separates the inside and the outside of the chamber for transplantation) between the inside and the outside thereof. The membrane for immunoisolation includes a porous membrane containing a polymer.

<Membrane for Immunoisolation>

In the present specification, a membrane for immunoisolation refers to a membrane used for immunoisolation.

Immunoisolation is one of a method for preventing an immune rejection by a recipient in a case of transplantation. Here, the immune rejection is a rejection by a recipient with respect to a biological constituent to be transplanted. A biological constituent is isolated from an immune rejection by a recipient due to immunoisolation. Examples of immune rejections include reactions based on cellular immune responses and reactions based on humoral immune responses.

The membrane for immunoisolation is a selectively permeable membrane that allows nutrients such as oxygen, water, and glucose to permeate therethrough, and inhibits permeation of immune cells and the like involved in an immune rejection. Examples of immune cells include macrophages, dendritic cells, neutrophils, eosinophils, basophils, natural killer cells, various T cells, B cells, and other lymphocytes.

Depending on the application, the membrane for immunoisolation preferably inhibits permeation of high-molecular-weight proteins such as immunoglobulins (IgM, IgG, and the like) and complements, and preferably allows a relatively low-molecular-weight physiologically active substances such as insulin to permeate therethrough.

The selective permeability of the membrane for immunoisolation may be adjusted according to the application. The membrane for immunoisolation may be a selectively permeable membrane which blocks a substance having a molecular weight such as 500 kDa or more, 100 kDa or more, 80 kDa or more, or 50 kDa or more. For example, it is preferable that the membrane for immunoisolation be capable of inhibiting permeation of the smallest IgG (molecular weight of about 160 kDa) among antibodies. In addition, the membrane for immunoisolation may be a selectively permeable membrane which blocks a substance having a diameter such as 500 nm or more, 100 nm or more, 50 nm or more, or 10 nm or more, as a sphere size.

The chamber for transplantation according to the embodiment of the present invention includes one or more membranes for immunoisolation in a boundary between the inside and the outside of the chamber for transplantation. The membrane for immunoisolation may be formed of only the porous membrane or may contain other layers such as a hydrogel membrane. At least one surface of the membrane for immunoisolation is preferably the porous membrane, and it is also preferable that the membrane for immunoisolation be formed of the porous membrane.

A thickness of the membrane for immunoisolation is not particularly limited, but it is preferably 10 μm or more. In addition, it is sufficient for the thickness of the membrane for immunoisolation to be 500 μm or less, and it is preferably 300 μm or less, is more preferably 200 μm or less, is even more preferably 100 μm or less, and is particularly preferably 50 μm or less.

[Porous Membrane]

(Structure of Porous Membrane)

The porous membrane is a membrane having a plurality of pores. Pores can be confirmed by, for example, captured images of a scanning electron microscope (SEM) or captured images of a transmission electron microscope (TEM) of a cross section of the membrane.

A thickness of the porous membrane is not particularly limited, but it is preferably 10 μm or more. In addition, it is sufficient for the thickness of the porous membrane to be 250 μm or less, and it is preferably 200 μm or less, is more preferably 100 μm or less, and is even more preferably 50 μm or less. By setting the thickness of the porous membrane to 10 μm or more, it is possible to obtain membrane hardness at which the chamber for transplantation does not break in a recipient. In addition, by setting the thickness of the porous membrane to 250 μm or less, it is possible to obtain the chamber for transplantation having stiffness to the extent that a recipient is not uncomfortable.

In the chamber for transplantation according to the embodiment of the present invention, the porous membrane has a layered compact portion where a pore diameter is the smallest within the membrane. In addition, a pore diameter continuously increases in a thickness direction from the compact portion toward both one surface A and the other surface B of the porous membrane. In the present specification, in the porous membrane, a surface which is on the outside of the chamber for transplantation is referred to as the surface A, and a surface which is on the inside of the chamber for transplantation is referred to as the surface B. A pore diameter is determined by an average pore diameter of a parting line of a cross section of the membrane which will be described later.

The surface of the membrane means a main surface (a front surface or a back surface showing an area of the membrane), and does not mean a surface in the thickness direction of an end of the membrane. The surface of the porous membrane may be an interface with another layer. In the membrane for immunoisolation, it is preferable that the porous membrane have the same structure in an intra-membrane direction (a direction parallel to the membrane surface) with respect to pore diameters or pore diameter distribution (a difference in pore diameters in the thickness direction).

With the porous membrane having pore diameter distribution in the thickness direction, the life of the chamber for transplantation according to the embodiment of the present invention can be improved. The reason is that, by using a plurality of membranes having substantially different pore diameters, effects are obtained as though multistage filtration would be carried out, and therefore a deterioration in the membrane can be prevented.

A pore diameter may be measured from a photograph of a cross section of the membrane obtained by an electron microscope. The porous membrane can be cut with a microtome or the like, and it is possible to obtain a photograph of a cross section of the porous membrane as a section of a thin membrane which a cross section can be observed.

In the present specification, the comparison of pore diameters in the thickness direction of the membrane is performed by comparing pore diameters in 19 parting lines in a case where an SEM image of the cross section of the membrane is divided into 20 in the thickness direction of the membrane. 50 or more consecutive pores that intersect or are in contact with the parting line are selected, each of the pore diameters is measured, and an average value is calculated as an average pore diameter. Here, as the pore diameter, not a length of a portion where the selected pore intersects the parting line, but a diameter is used, the diameter being calculated using an area, which is obtained by calculating an area of pores calculated from an SEM image of the cross section of the membrane by image processing, as an area of a true circle. In this case, for a parting line in which pores are large and therefore only up to 50 pores can be selected, an average pore diameter is assumed to an average pore diameter obtained by measuring 50 pores by broadening the field of view of an SEM image for obtaining the cross section of the membrane. Pore diameters in the thickness direction of the membrane are compared by comparing the obtained average pore diameter for each parting line.

The layered compact portion having the smallest pore diameter refers to a layered portion of the porous membrane including the parting line where an average pore diameter becomes the smallest among parting lines in a photograph of the cross section of the membrane. The compact portion may include two or more parting lines. For example, in a case where two or more parting lines, which have an average pore diameter 1.1 times or less the minimum average pore diameter, are consecutive, the compact portion is assumed to include two or more consecutive parting lines. In the present specification, a thickness of the compact portion is a product of the number of parting lines included in the compact portion and one-twentieth of the thickness of the membrane.

In the present specification, an average pore diameter of the compact portion is denoted as the minimum pore diameter of the porous membrane. The minimum pore diameter of the porous membrane is preferably 0.02 μm to 1.5 μm, and is more preferably 0.02 μm to 1.3 The reason is that the minimum pore diameter of such a porous membrane can inhibit permeation of at least normal cells. An average pore diameter of the compact portion is measured by ASTM F316-80.

The porous membrane has a compact portion within the membrane. The phrase "within the membrane" means that the compact portion is not in contact with the surface of the membrane. The phrase "having the compact portion within the membrane" means that the compact portion is not a portion that contains the parting line closest to any surface of the membrane. By using the porous membrane having a structure having the compact portion within the membrane, permeability of a substance intended to permeate is unlikely to lower compared to a case of using a porous membrane having the compact portion, which is in contact with the surface thereof. Although not bound by any theory, it is perceived that protein adsorption is less likely to occur due to the presence of the compact portion within the membrane.

It is preferable that the compact portion be biased to one of the front surface side than a central portion in thickness of the porous membrane. Specifically, the compact portion is preferably located between any one surface of the porous membrane and a portion at a distance of less than half the thickness of the porous membrane from the surface, and it is more preferably located between any one surface of the porous membrane and a portion at a distance of two-fifths of the thickness of the porous membrane from the surface. This distance may be determined from the photograph of the cross section of the membrane described above. In the present specification, the surface of the porous membrane closer to the compact portion is referred to as a "surface X." It is preferable that the surface X be the surface B (a surface which is on the inside of the chamber for transplantation). The reason is that, since the compact portion is disposed closer to the enclosed biological constituent, a neutral point of stress at the time of deformation of the chamber for transplantation is also located on the biological constituent side, and thereby stress applied to the biological constituent can be suppressed. Another reason is that it is possible to make permeability of physiologically active substances higher.

In the porous membrane of the chamber for transplantation according to the embodiment of the present invention, a pore diameter continuously increases in the thickness direction from the compact portion toward both one surface A and the other surface B of the porous membrane. The sentence "the pore diameter continuously increases in the thickness direction" means that a difference in average pore diameters between the above-mentioned parting lines adjacent to each other in the thickness direction increases by 50% or less of a difference between maximum average pore diameters (maximum pore diameter) and minimum average pore diameters (minimum pore diameter), preferably increases by 40% or less, and more preferably increases by 30% or less. The phrase "continuously increasing" essentially means that a pore diameter increases uniformly without decreasing, but a decreasing portion may occur accidentally. For example, in a case where each of two parting lines of an SEM image of a cross section of the membrane which is an image used for comparison of pore diameters in the thickness direction of the membrane is combined from the surface, and in a case where an average value of an average pore diameter of the combined parting lines increases uniformly (uniformly decreases toward the compact portion from the surface), it can be determined that "the pore diameter continuously increases in the thickness direction toward the surface of the membrane from the compact portion."

A structure of the porous membrane in which a pore diameter continuously increases in the thickness direction can be realized by, for example, a manufacturing method to be described later.

In the present specification, in the SEM image of the cross section of the membrane used for comparison of pore diameters in the thickness direction of the membrane, the average pore diameter at a parting line closest to the surface A of the porous membrane is referred to as an average pore diameter of the surface A, and the average pore diameter at a parting line closest to the surface B of the porous membrane is referred to as an average pore diameter of the surface B. In the chamber for transplantation according to the embodiment of the present invention, an average pore diameter of the surface A is larger than an average pore diameter of the surface B. In a case where the surface A, that is, a surface on the cell side of the recipient at the time of using the chamber for transplantation, has a larger pore diameter, formation of new blood vessels, that is, angiogenesis is likely to occur based thereon. For this reason, the supply of oxygen or the like to the biological constituent enclosed in the chamber for transplantation is stabilized, and necrosis or the like of the biological constituent is unlikely to occur.

It is sufficient for an average pore diameter of the surface A to be 0.15 μm or more, and it is preferably 1.0 μm to 100 μm, is more preferably 1.5 μm to 50 μm, and is even more preferably 2.0 μm to 25 μm. It is sufficient for an average pore diameter of the surface B to be 0.05 μm or more, and it is preferably 0.1 μm to 10 μm, is more preferably 0.2 μm to 5.0 μm, and is even more preferably 0.5 μm to 2.5 μm. In addition, an average pore diameter of the surface A is preferably 1.5 times or more, is more preferably 2 times or more, and is even more preferably 3 times or more an average pore diameter of the surface B. In addition, an average pore diameter of the surface A is preferably 10 times or less and is more preferably is 8 times or less an average pore diameter of the surface B. Within such an average pore diameter range, the porous membrane can be more stably produced.

In the present specification, an average pore diameter of the parting line having the maximum average pore diameter among parting lines is referred to as the maximum pore diameter of the porous membrane. A maximum pore diameter of the porous membrane is preferably 0.15 μm to 100 μm, is more preferably 1.0 μm to 50 μm, and is even more preferably 2.0 μm to 21 μm. In the porous membrane of the chamber for transplantation according to the embodiment of the present invention, it is preferable that the surface A have the maximum pore diameter.

A ratio of an average pore diameter of the compact portion to the maximum pore diameter of the porous membrane (a ratio of a minimum pore diameter to a maximum pore diameter of the porous membrane, which is a value obtained by dividing the maximum pore diameter by the minimum pore diameter, an "anisotropy ratio" in the present specification) is preferably 3 or more, is more preferably 4 or more, and is even more preferably 5 or more. The reason is that an average pore diameter except for that of the compact portion increases to increase substance permeability of the porous membrane. In addition, the anisotropy ratio is preferably 25 or less and is more preferably 20 or less. The reason is that effects, as though multistage filtration would be carried out, can be efficiently obtained within a range where an anisotropy ratio is 25 or less.

In the chamber for transplantation according to the embodiment of the present invention, a porosity in a vicinity of the surface A is 65% or more. With the surface A having such a porosity, angiogenesis in tissue of a recipient is likely to be induced on the outside of the chamber for transplantation which is the surface A side. In the present specification, the vicinity of the surface A represents a portion from the surface A to one-fifth of the thickness of the porous membrane. The porosity may be obtained from a density in the vicinity of the surface A, and is specifically a value obtained by the procedure described in Examples. The porosity in the vicinity of the surface A is preferably 67% or more and is more preferably 70% or more. The porosity in the vicinity of the surface A is usually 90% or less. By setting the porosity to 90% or less, the required strength of the porous membrane is maintained, and thereby it is possible to prevent damage of the chamber for transplantation in the recipient or deformation of the pores which causes an inducement of angiogenesis or a deterioration in selective permeability.

(Elemental Distribution of Porous Membrane)

Formulas (I) and (II) are preferably satisfied for at least one surface of the porous membrane.

$$B/A \leq 0.7 \quad \text{(I)}$$

$$A \geq 0.015 \quad \text{(II)}$$

In the formula, A represents a ratio of an N element (nitrogen atom) to a C element (carbon atom) on a surface of the membrane, and B represents a ratio of the N element to the C element at a depth of 30 nm from the same surface.

Formula (II) shows that a certain amount or more of N element is present on at least one surface of the porous membrane, and Formula (I) shows that an N element in the porous membrane is localized at a depth of less than 30 nm of the surface.

With the surface satisfying Formulas (I) and (II), a bioaffinity of the porous membrane, particularly, a bioaffinity of the surface side satisfying Formulas (I) and (II) becomes high.

In the porous membrane, either one of surfaces may satisfy Formulas (I) and (II), or both surfaces may satisfy Formulas (I) and (II), but it is preferable that both surfaces satisfy Formulas (I) and (II). In a case where either one of surfaces satisfies Formulas (I) and (II), the surface thereof may be in an inside or an outside of a chamber for transplantation to be described later, but the surface is preferably in the inside thereof. In addition, in a case where only one of any surface satisfies Formulas (I) and (II) and the porous membrane has the above-mentioned surface X, a surface satisfying Formulas (I) and (II) is preferably the surface X.

In the present specification, a ratio (A value) of N element to C element on the membrane surface and a ratio (B value) of N element to C element at a depth of 30 nm from the surface are obtained by calculating using XPS measurement results. The XPS measurement is X-ray photoelectron spectroscopy, which is a method for irradiating a membrane surface with X-rays, measuring kinetic energy of photoelectrons emitted from the membrane surface, and analyzing a composition of elements constituting the membrane surface. Under conditions using a monochromated Al-Kα ray described in Examples, the A value is calculated from results at the start of sputtering, and the B value is calculated from time results, which are calculated that the ray is at 30 nm from the surface of the membrane measured from a sputtering rate.

B/A may be 0.02 or more, and is preferably 0.03 or more, and is more preferably 0.05 or more.

A is preferably 0.050 or more and is more preferably 0.080 or more. In addition, A may be 0.20 or less, and is preferably 0.15 or less, and is more preferably 0.10 or less.

B may be 0.001 to 0.10, and is preferably 0.002 to 0.08, and is more preferably 0.003 to 0.07.

In a method for manufacturing the porous membrane which will be described later, the elemental distribution of the porous membrane, especially the distribution of an N element, can be controlled by a moisture concentration contained in the temperature-controlled humid air, a time to apply the temperature-controlled humid air, a temperature of a coagulation liquid, an immersion time, a temperature of a diethylene glycol bath for washing, an immersion time in the diethylene glycol bath for washing, a speed of a porous membrane manufacture line, and the like. The distribution of the N element can also be controlled by an amount of moisture contained in a stock solution for forming a membrane.

(Composition of Porous Membrane)

The porous membrane contains a polymer. It is preferable that the porous membrane be essentially composed of a polymer.

The polymer forming the porous membrane is preferably biocompatible. Here, the term "biocompatible" means that the polymer has non-toxic and non-allergenic properties, but does not have properties such that the polymer is encapsulated in a living body.

The number average molecular weight (Mn) of the polymer is preferably 1,000 to 10,000,000, and is more preferably 5,000 to 1,000,000.

Examples of polymers include thermoplastic or thermosetting polymers. Thermoplastic polymers are preferable. Specific examples of the polymer include polysulfone, cellulose acylate such as cellulose acetate, nitrocellulose, sulfonated polysulfone, polyethersulfone, polyvinylidene fluoride, polyacrylonitrile, styrene-acrylonitrile copolymer, styrene-butadiene copolymer, saponified ethylene-vinyl acetate copolymer, polyvinyl alcohol, polycarbonate, an organosiloxane-polycarbonate copolymer, a polyester carbonate, an organopolysiloxane, a polyphenylene oxide, a polyamide, a polyimide, polyamideimide, polybenzimidazole, ethylene vinyl alcohol copolymer, polytetrafluoroethylene (PTFE), and the like. From the viewpoints of solubility, optical physical properties, electrical physical properties, strength, elasticity, and the like, polymers may be homopolymers, copolymers, polymer blends, or polymer alloys.

Among them, polysulfone, polyethersulfone, and cellulose acylate are preferable, and polysulfone is more preferable.

In a case where polysulfone or polyethersulfone is used as the polymer, the porous membrane preferably further contains a hydrophilic polymer. Examples of hydrophilic polymers include polyvinylpyrrolidone, hydroxypropyl cellulose, hydroxyethyl cellulose, and the like. Among them, polyvinylpyrrolidone is preferable. By combining polysulfone or polyethersulfone which are hydrophobic with the hydrophilic polymer, biocompatibility can be improved.

The porous membrane may contain other components other than the above-mentioned components as an additive.

Examples of additives include metal salts of inorganic acids such as sodium chloride, lithium chloride, sodium nitrate, potassium nitrate, sodium sulfate, and zinc chloride; metal salts of organic acids such as sodium acetate and sodium formate; other polymers such as polyethylene glycol; high polymer electrolytes such as sodium polystyrene sulfonate and polyvinyl benzyl trimethyl ammonium chloride; ionic surfactants such as sodium dioctyl sulfosuccinate and sodium alkyl sodium taurate; and the like. The additive may act as a swelling agent for a porous structure. As an additive, it is preferable to use a metal salt. The porous membrane containing polysulfone or polyethersulfone preferably contains lithium chloride.

The porous membrane is preferably a membrane formed from a single composition as a single layer, and preferably not has a laminated structure of a plurality of layers. By forming the porous membrane from one composition as a single layer, it is possible to manufacture the chamber for transplantation at low costs by a simple procedure.

(Method for Manufacturing Porous Membrane)

A method for manufacturing the porous membrane is not particularly limited as long as the method can form the porous membrane having the above-mentioned structure, and any general methods for forming a polymer membrane can be used. Examples of methods for forming a polymer membrane include a stretching method, a flow-casting method, and the like, and a flow-casting method is preferable.

For example, in the flow-casting method, it is possible to produce a porous membrane having the above-mentioned structure by adjusting the type and amount of a solvent used in a stock solution for forming a membrane, and a drying method after flow-casting.

Manufacture of a porous membrane by using a flow-casting method can be carried out by a method including, for example, the following (1) to (4) in this order.

(1) A stock solution for forming a membrane, which contains a polymer, if necessary an additive and, if necessary a solvent, is flow-cast on a support while being in a dissolved state.

(2) The surface of the flow-cast liquid membrane is exposed to temperature-controlled humid air.

(3) The membrane obtained after being exposed to temperature-controlled humid air is immersed in a coagulation liquid.

(4) A support is peeled off if necessary.

A temperature of temperature-controlled humid air may be 4° C. to 60° C. and is preferably 10° C. to 40° C. A relative humidity of the temperature-controlled humid air may be 15% to 100% and is preferably 25% to 95%. The temperature-controlled humid air may be applied at a wind speed of 0.1 m/s to 10 m/s for 0.1 seconds to 30 seconds, preferably 1 second to 10 seconds.

In addition, an average pore diameter and position of the compact portion can also be controlled by a moisture concentration contained in the temperature-controlled humid air and a time of applying the temperature-controlled humid air. An average pore diameter of the compact portion can also be controlled by an amount of moisture contained in a stock solution for forming a membrane.

By applying the temperature-controlled humid air to the surface of the liquid membrane as described above, it is possible to cause coacervation from the surface of the liquid membrane toward the inside of the membrane by controlling evaporation of a solvent. By immersing the membrane in a coagulation liquid containing a solvent having low solubility of the polymer but compatible with the solvent of the polymer in this state, the above-mentioned coacervation phase is fixed as fine pores, and pores other than the fine pores can also be formed.

A temperature of the coagulation liquid may be −10° C. to 80° C. in a process of immersing the membrane in the coagulation liquid. By changing a temperature during this period, it is possible to control a size of a pore diameter up to a support surface side by adjusting a time from the formation of the coacervation phase on the support surface side to the solidification from the compact portion. In a case where a temperature of the coagulation liquid is raised, the formation of the coacervation phase becomes faster and a time for solidification becomes longer, and therefore the pore diameter toward the support surface side tends to become large. On the other hand, in a case where a temperature of the coagulation liquid is lowered, the formation of the coacervation phase becomes slower and a time for solidification becomes shorter, and therefore the pore diameter toward the support surface side is unlikely to become large.

As the support, a plastic film or a glass plate may be used. Examples of materials of the plastic film include polyester such as polyethylene terephthalate (PET), polycarbonate, acrylic resin, epoxy resin, polyurethane, polyamide, polyolefin, a cellulose derivative, silicone, and the like. As the support, a glass plate or PET is preferable, and PET is more preferable.

The stock solution for forming a membrane may contain a solvent. A solvent having high solubility of the polymer to be used (hereinafter referred to as "favorable solvent") may be used depending on a polymer to be used. As a favorable solvent, it is preferable that the solvent be quickly substituted with the coagulation liquid in a case where the membrane is immersed in the coagulation liquid. Examples of solvents include N-methyl-2-pyrrolidone, dioxane, tetrahydrofuran, dimethylformamide, dimethylacetamide, or a mixed solvent thereof in a case where the polymer is polysulfone and the like; dioxane, N-methyl-2-pyrrolidone, dimethylformamide, dimethylacetamide, dimethylsulfoxide, or a mixed solvent thereof in a case where the polymer is polyacrylonitrile and the like; dimethylformamide, dimethylacetamide, or a mixed solvent thereof in a case where the polymer is polyamide and the like; acetone, dioxane, tetrahydrofuran, N-methyl-2-pyrrolidone, or a mixed solvent thereof in a case where the polymer is cellulose acetate and the like. Among them, N-methyl-2-pyrrolidone is preferably used.

In addition to a favorable solvent, the stock solution for forming a membrane preferably use a solvent (hereinafter referred to as "non-solvent") in which the solubility of the polymer is low but is compatible with the solvent of the polymer. Examples of non-solvents include water, cellosolves, methanol, ethanol, propanol, acetone, tetrahydrofuran, polyethylene glycol, glycerin, and the like. Among these, it is preferable to use water.

A concentration of the polymer as the stock solution for forming a membrane may be 5 mass % to 35 mass %, is preferably 10 mass % to 30 mass %. By setting the concentration thereof to 35 mass % or less, sufficient permeability (for example, water permeability) can be imparted to the obtained porous membrane. By setting the concentration thereof to 5 mass % or more, the formation of a porous membrane which selectively allows substances to permeate can be secured. An amount of additive to be added is not particularly limited as long as the homogeneity of the stock solution for forming a membrane is not lost by the addition, but is 0.5% by volume to 10% by volume respect to a general solvent. In a case where the stock solution for forming a membrane contains a non-solvent and a favorable solvent, a ratio of the non-solvent to the favorable solvent is not particularly limited as long as a mixed solution can be maintained in a homogeneous state, but is preferably 1.0 mass % to 50 mass %, is more preferably 2.0 mass % to 30 mass %, and is even more preferably 3.0 mass % to 10 mass %.

In addition, in the stock solution for forming a membrane for manufacturing a porous membrane containing a polymer selected from the group consisting of polysulfone and polyethersulfone, and containing polyvinylpyrrolidone, polyvinylpyrrolidone is preferably contained by an amount of 50 mass % to 120 mass %, and more preferably by an amount of 80 mass % to 110 mass %, with respect to a total mass of polysulfone and polyethersulfone. Furthermore, in a case where the stock solution for forming a membrane contains lithium chloride as an additive, lithium chloride is preferably contained by an amount of 5 mass % to 20 mass %, and more preferably by 10 mass % to 15 mass %, with respect to the total mass of polysulfone and polyethersulfone.

As the coagulation liquid, it is preferable to use a solvent having a low solubility of the polymer used. Examples of such solvents include water, alcohols such as methanol, ethanol, and butanol; glycols such as ethylene glycol and diethylene glycol; aliphatic hydrocarbons such as ether, n-hexane, and n-heptane; glycerol such as glycerin; and the like. Examples of preferred coagulation liquids include water, alcohols, or a mixture of two or more of these. Among these, it is preferable to use water.

After immersion in the coagulation liquid, it is also preferable to perform washing with a solvent different from the coagulation liquid that has been used. Washing can be carried out by immersing in a solvent. Diethylene glycol is preferable as a washing solvent. Distribution of an N element in the porous membrane can be adjusted by adjusting either or both of a temperature and an immersion time of diethylene glycol in which a film is immersed by using diethylene glycol as a washing solvent. In particular, in a case where polyvinylpyrrolidone is used as the stock solution for forming a membrane of the porous membrane, a residual amount of polyvinylpyrrolidone on the membrane can be controlled. After washing with diethylene glycol, furthermore, the membrane may be washed with water.

Regarding a method for manufacturing the porous membrane, reference can be made to JP1992-349927A (JP-H04-349927A), JP1992-068966B (JP-H04-068966B), JP1992-351645A (JP-H04-351645A), JP2010-235808A, and the like.

[Other Layers]

The membrane for immunoisolation may contain layers other than the porous membrane.

Examples of other layers include a hydrogel membrane. As a hydrogel membrane, a biocompatible hydrogel membrane is preferable. Examples thereof include an alginic acid gel membrane, an agarose gel membrane, a polyisopropyl acrylamide membrane, a membrane containing cellulose, a membrane containing a cellulose derivative (for example, methyl cellulose), a polyvinyl alcohol membrane, or the like. The hydrogel membrane is preferably an alginic acid gel membrane. Specific examples of alginic acid gel membranes include a polyion complex membrane of alginic acid-poly-L-lysine-alginic acid.

<Structure and the Like of Chamber for Transplantation>

The membrane for immunoisolation is disposed on at least part of a boundary between the inside and the outside of the chamber for transplantation. By disposing in such a manner, it is possible to protect the biological constituent enclosed in the chamber for transplantation from immune cells and the like present outside, and to introduce nutrients such as water, oxygen, and glucose into the inside of the chamber for transplantation from the outside.

The membrane for immunoisolation may be disposed on the entire surface of the boundary forming the inside and the outside of the chamber for transplantation, and may be disposed a part of the surface corresponding to an area of, for example, 1% to 99%, 5% to 90%, 10% to 80%, 20% to 70% %, 30% to 60%, 40% to 50%, or the like with respect to the entire area. The membrane for immunoisolation is preferably disposed on substantially the entire surface of the boundary between the inside and the outside of the chamber for transplantation. A surface on which the membrane for immunoisolation is disposed may be one continuous portion or may be divided into two or more portions.

In a case where the membrane for immunoisolation is not disposed on the entire surface of the boundary forming the inside and the outside of the chamber for transplantation, it is sufficient that remaining portions are formed of a material such as an impermeable membrane not allowing permeation of nutrients such as oxygen, water, and glucose, in addition to cells and the like.

The chamber for transplantation may have a joint portion at which the membranes for immunoisolation face each other to be joined. A portion of the membrane for immunoisolation that is being joined is not particularly limited, but it is preferably an end portion of the membrane for immunoisolation. In particular, it is preferable that end portions be joined to each other. In the present specification, in a case where the term "end portion" is used regarding the membrane, it means a peripheral portion or a part thereof having a constant width which is substantially in contact with the side surface (edge) of the membrane thickness. It is preferable that all of outer peripheries except an injection port and the like to be described later be joined to each other between the membranes for immunoisolation. For example, the chamber for transplantation preferably has a configuration in which two membranes for immunoisolation face each other and outer peripheries thereof are joined, or a configuration in which one membrane for immunoisolation having a line symmetric structure is folded into two and facing outer peripheries are joined.

Joining can be performed by adhesion using an adhesive, fusion welding, and the like. For example, the surface B's can be faced with each other to be adhered by using a curable adhesive. Examples of adhesives include known adhesives such as epoxy-based adhesives, silicone-based adhesives, acrylic-based adhesives, and urethane-based adhesives.

In addition, the surface B's may be faced with each other to be joined by sandwiching a thermoplastic resin between the porous membranes and heating this portion. In this case, as the thermoplastic resin, a resin having a melting point lower than that of the polymer forming the porous membrane is preferably used. Specific examples of thermoplastic resins include polyethylene, polypropylene, polyurethane, polyvinyl chloride, polytetrafluoroethylene, polyethylene terephthalate, polycarbonate, and the like. Among them, polyethylene, polypropylene, polyurethane, polyvinyl chloride, and polytetrafluoroethylene are preferable, and polyethylene, polyurethane, and polyvinyl chloride are more preferable.

Furthermore, the porous membranes in the membrane for immunoisolation may be fusion welded in a state where the surface B's are directly in contact with each other without sandwiching another material between the porous membranes. By such fusion welding, it is possible to obtain a chamber for transplantation not having a problem derived from a resin sandwiched between the porous membranes or the like. In a case of using porous membranes which contain a polymer selected from the group consisting of polysulfone and polyethersulfone, the porous membranes can be fusion welded to each other to be integrated by heating them at a temperature of a glass transition temperature or higher of the polymer and lower than a melting point of the polymer. Specifically, regarding the heating for the fusion welding, it is sufficient for a temperature to be 190° C. or higher and lower than 340° C., and a temperature is preferably 230° C. or higher and lower than 340° C.

A shape of the chamber for transplantation is not limited, and may be a shape such as a pouched-like shape, a bag shape, a tube shape, a microcapsule shape, or a drum shape. For example, a drum-shaped chamber for transplantation can be formed by joining the membrane for immunoisolation to the top and bottom of a silicone ring. A shape of the chamber for transplantation is preferably a shape capable of preventing movement of the chamber for transplantation within a recipient in a case where the chamber for transplantation is used as a device for transplantation to be described later. Specific examples of shapes of the chamber for transplantation include a cylindrical shape, a disk-like shape, a rectangular shape, an egg shape, a star shape, a circular shape, and the like. The chamber for transplantation may be in a form of a sheet, a strand, a spiral, or the like. The chamber for transplantation may be a chamber for transplantation which encloses the biological constituent and becomes the above-described shape only in a case where the chamber for transplantation used as a device for transplantation to be described later.

The chamber for transplantation may contain a biocompatible plastic or the like for maintaining the shape and strength as a container. For example, the boundary between the inside and the outside of the chamber for transplantation may be made from a porous membrane and a biocompatible plastic. In addition, in the chamber for transplantation of which the porous membrane is disposed on the entire surface of the boundary between the inside and the outside, a biocompatible plastic having a net-like structure may be further disposed on the outside of the boundary between the inside and the outside, from the viewpoint of strength.

<Injection Port>

The chamber for transplantation preferably includes an injection port or the like for injecting the biological constituent or the like into the chamber for transplantation. As the injection port, a tube communicating with the inside of the chamber for transplantation may be provided.

The tube may contain a thermoplastic resin, for example. The thermoplastic resin preferably has a melting point which is lower than that of the polymer material of the porous membrane.

Specific examples of thermoplastic resins used in the tube include polyethylene, polypropylene, polyurethane, polyvinyl chloride, polytetrafluoroethylene, polyethylene terephthalate, polycarbonate, and the like. Among them, polyethylene, polypropylene, polyurethane, polyvinyl chloride, and polytetrafluoroethylene are preferable, and polyethylene, polyurethane, and polyvinyl chloride are particularly preferable.

For example, the tube is sandwiched between the membranes for immunoisolation in a manner of coming into contact with a part of the porous membrane, and thereby joining with the part thereof. Joining can be performed by heat fusion welding, adhesion using an adhesive, and the like. Among them, it is preferable to perform heat fusion welding.

In a case of performing heat fusion welding, the tube preferably contains a thermoplastic resin having a melting point which is lower than that of the polymer material of the porous membrane. The reason is that, in a case of performing heat fusion welding between the porous membrane and a tube containing a thermoplastic resin having a melting point which is lower than that of the polymer material of the porous membrane, the tube material is considered to be first melted at the time of heating so that the melted tube material can get into the pores of the porous membrane.

In a case of performing adhesion, adhesives such as epoxy-based adhesives, silicone-based adhesives, acrylic-based adhesives, and urethane-based adhesives can be used as the adhesive. For example, in a case where a tube containing a resin material having a melting point lower than that of the polymer material of the porous membrane is used, joining can be performed by adhesion.

<Application of Chamber for Transplantation>

The chamber for transplantation encloses the biological constituent and is used for transplantation of the biological constituent into the recipient. By using the chamber for transplantation, it is possible to prevent an immune rejection of the recipient with respect to the transplanted biological constituent. That is, the membrane for immunoisolation can be used for protecting biological constituents from an immune system of a recipient. In the present specification, a recipient means a living body to which transplantation is performed. A recipient is preferably a mammal and is more preferably a human.

[Biological Constituent]

The biological constituent means a structure body derived from a living body. Examples of living bodies include viruses, bacteria, yeasts, fungal cells, insects, plants, mammals, and the like. It is preferable that a living body be generally a mammal Examples of mammals include bovines, swine, sheep, cats, dogs, humans, and the like. The biological constituent is preferably a structure body derived from any of mammals.

Examples of biological constituents include organs, tissues, cells, and the like. Among these, cells are preferable as biological constituents. As cells, a single cell may be used or a plurality of cells may be used. It is preferable that a plurality of cells be used. A plurality of cells may be separated from each other or may be an aggregate.

The biological constituent may be obtained directly from a living body. In addition, particularly in a case where the biological constituent is a cell, the biological constituent may be directly obtained from a living body, or may be obtained by differentiation-induction of cells such as embryonic stem cells (ES cell), induced pluripotent stem cells (iPS cell), and mesenchymal stem cells. The cell may be a progenitor cell.

As a biological constituent, as one aspect, it is preferable to release a physiologically active substance. Examples of physiologically active substances include various hormones, various cytokines, various enzymes, and various other biologic factors in a living body. More specific examples include insulin, dopamine, factor VIII, and the like.

Here, insulin is a polypeptide (molecular weight of about 6000) in which an A chain of 21 amino acid residues and a B chain of 30 amino acid residues are linked via a disulfide bond. In insulin in a living body of a mammal is secreted from β cells in pancreatic islets of Langerhans. In a case of using insulin-secreting cells as the biological constituent in the present invention, insulin secreted may be human-type insulin or other mammalian-type (for example, porcine-type) insulin. Insulin may be insulin produced by a genetic recombination method. As a method for obtaining genetically modified insulin, for example, the description of Kadowaki Takashita: Diabetes Navigator (refer to 270-271, Takeo Tao, Yoshikazu Oka "Insulin Preparations of Present and Future," Medical Review, 2002) can be referred to. Various types of insulin analogues (refer to, for example, H. C. Lee, J. W. Yoon, et al., Nature, 408, 483-488, 2000) may be used.

The biological constituent is preferably an insulin-secreting cell. Insulin-secreting cells are cells that can secrete insulin in response to changes in blood glucose level. The insulin-secreting cells are not particularly limited. Examples thereof include pancreatic β cells present in pancreatic islets of Langerhans. Pancreatic β cells may be human pancreatic β cells, or may be pancreatic β cells such as pigs and mice.

For a method for extracting pancreatic β cells from a pig, reference can be made to the description in JP2007-195573A. In addition, the insulin-secreting cells may be cells derived from human stem cells (refer to, for example, Junichi Miyazaki, Regenerative Medicine, Vol. 1, No. 2, pp. 57-61, 2002), or cells derived from small intestinal epithelial stem cells (refer to, for example, Fumikomi Mineko et al., Regenerative Medicine, Volume 1, No. 2, pp. 63 to 68, 2002), or insulin-secretory cells into which a gene encoding insulin has been incorporated (refer to, for example, H. C. Lee, J. W. Yoon, et al., Nature, 408, pp. 483-488, 2000). Furthermore, the insulin-secreting cells may be pancreatic islets of Langerhans (refer to, for example, Horiyama, Kazumori Inoue, Regenerative Medicine, Volume 1, No. 2, pp. 69 to 77, 2002).

<<Device for Transplantation>>

The device for transplantation is a complex including at least a chamber for transplantation and a biological constituent. In the device for transplantation, the chamber for transplantation encloses the biological constituent therein.

In the device for transplantation, the chamber for transplantation may enclose only the biological constituent therein, or may enclose the biological constituent, and constituents or components other than the biological constituent therein. For example, the biological constituent may be enclosed in the chamber for transplantation together with a hydrogel, and preferably in a state of being enclosed in the hydrogel. In addition, the device for transplantation may contain pH buffers, inorganic salts, organic solvents, proteins such as albumin, or peptides.

The device for transplantation may contain only one biological constituent or may contain two or more biological constituents. For example, the device for transplantation may contain only a biological constituent which releases physiologically active substances for the purpose of transplantation, or which serves other functions of transplantation; or may further contain a biological constituent assisting functions of these biological constituents.

The device for transplantation may be, for example, a device to be transplanted intraperitoneally or subcutaneously. In addition, the device for transplantation may be a blood-vessel-connecting device. For example, in a case where insulin-secreting cells are used as the biological constituent, insulin secretion corresponding to a change in blood glucose level becomes possible by performing transplantation such that blood and a membrane come into direct contact with each other.

Regarding the device for transplantation and chamber for transplantation, the description of Protein Nucleic Acid Enzyme, Vol. 45, pp. 2307 to 2312, (Okawara Hisako, 2000), JP2009-522269A, JP1994-507412A (JP-H06-507412A), and the like can be referred to.

EXAMPLES

Characteristics of the present invention will be described in more detail with reference to the following examples and comparative examples. The materials, amounts used, proportions, treatment details, treatment procedures, and the like disclosed in the following Examples can be modified as appropriate as long as the gist of the present invention is maintained. Therefore, the scope of the present invention should not be limitedly interpreted by the specific examples described below.

<Production of Chamber for Transplantation and Porous Membrane>

Examples 1 to 8, Comparative Example 1

18 parts by mass of polysulfone (P3500 manufactured by Solvay), 12 parts by mass of polyvinylpyrrolidone (K-30), 0.5 parts by mass of lithium chloride, and 1.0 parts by mass of water were dissolved in 68.5 parts by mass of N-methyl-2-pyrrolidone. Thereby, a stock solution for forming a membrane was obtained. This stock solution for forming a membrane was flow-cast on a surface of a PET film such that a product thickness became 45 μm. The flow-cast membrane surface was exposed to air adjusted to 25° C. and relative humidity 40% RH, at 1 m/sec for 5 seconds. Immediately thereafter, the exposed membrane surface was immersed in a coagulation liquid tank filled with water at 30° C. PET was peeled off, and thereby a porous membrane was obtained. Thereafter, the immersed membrane surface was put into a diethylene glycol bath at 25° C. for 120 seconds, was thoroughly washed with pure water, and then was dried. Thereby, a porous membrane of Example 1 was obtained.

In addition, porous membranes of Examples 2 to 8 and Comparative Example 1 were produced in the same manner as the membrane of Example 1 by controlling a pore diameter and a thickness of the porous membranes to be values shown in Table 1 through adjustment of the thickness of the flow-cast stock solution for forming a membrane, the temperature and relative humidity of temperature-controlled humid air after flow-cast, and the temperature of the coagulation liquid tank.

Each porous membrane was folded into two so that the surface having a smaller average pore diameter faced with each other, and direct heat fusion welding was performed on outer edges thereof at 220° C. Thereby, chambers for transplantation of Examples 1 to 8 and Comparative Example 1 were produced. An average pore diameter of the surface was determined by a parting line closest to the surface among parting lines to be described later.

In Examples and Comparative Examples, a surface of the porous membrane which became the outside of the chamber for transplantation is referred to as a "surface A" and a surface on the side opposite thereto is referred to as a "surface B."

Example 9

—Production of Polytetrafluoroethylene Film—

20 parts by mass of a hydrocarbon oil ("Isopar M," manufactured by Exxon Mobil Corporation) as an extrusion auxiliary was added to 100 parts by mass of polytetrafluoroethylene fine powder ("POLYFLON PTFE F104U", manufactured by DAIKIN INDUSTRIES, LTD.) having a number average molecular weight of 6,200,000 as a crystalline polymer, and the mixture was subjected to paste extrusion to have a round bar shape. The round bar was subjected to calender operation at a rate of 50 m/min with a calender roll heated to 60° C. Thereby, a polytetrafluoroethylene film was produced. The obtained film was dried by being passed through a hot air drying oven at 250° C. to dry and remove the extrusion auxiliary. Thereby, a roll-shaped polytetrafluoroethylene film having an average thickness of 100 μm, an average width of 150 mm, and a specific gravity of 1.55 was produced.

—Production of Semi-Heated Film—

Conditions were set in advance, in which a temperature of one surface of the obtained polytetrafluoroethylene film became 360° C. by near infrared rays of a halogen heater having a built-in tungsten filament, on a roll (surface material SUS316) at 50° C. Subsequently, while blowing cooling air at 10° C. and at a flow rate of 500 L/min, the film was irradiated with near infrared rays of the same condition for 1 minute (asymmetric heating treatment). Thereby, a semi-heated film was produced. During the treatment, the surface temperature of the film was kept at 50° C.

—Production of Polytetrafluoroethylene Porous Membrane—

The obtained semi-heated film was stretched between rolls at 270° C. so as to be stretched 12.5 times in a longitudinal direction and was once wound on a winding roller. Thereafter, the film was preheated at 305° C. and then was stretched at 270° C. so as to be stretched 30 times in a width direction while both ends were clipped. Thereafter, heat fixation was performed at 380° C. An area stretching ratio of the obtained stretching film was 260 times in an elongation area ratio. Based on the above method, a polytetrafluoroethylene (PTFE) porous membrane having a compact portion within the membrane of Example 9 was obtained.

The polytetrafluoroethylene porous membrane was folded into two by facing surfaces having a smaller pore diameter, a polyethylene film (LIX (registered trade name) film manufactured by TOYOBO Co., Ltd., 50 μm) was sandwiched between only the outer edges of the surfaces, and then the outer edges were heat fusion welded at 200° C. Thereby, a chamber for transplantation of Example 9 was produced.

Comparative Examples 2 and 3

12 parts by mass of polysulfone (P3500 manufactured by Solvay), 12 parts by mass of polyvinylpyrrolidone (K-30), and 13 parts by mass of glycerin were dissolved in 63 parts by mass of N-methyl-2-pyrrolidone. Thereby, a stock solution for forming a membrane was obtained. This stock solution for forming a membrane was flow-cast on a surface of a PET film such that a product thickness became 50 μm. Immediately thereafter, the exposed membrane surface was immersed in a coagulation liquid tank filled with water at 30° C. PET was peeled off, and thereby a porous membrane was obtained. Thereafter, the immersed membrane surface was put into a diethylene glycol bath at 25° C. for 120 seconds, was thoroughly washed with pure water, and then was dried. Thereby, polysulfone porous membranes of Comparative Examples 2 and 3 in which a pore diameter continuously increases from one surface were obtained.

The polysulfone porous membrane was folded into two by facing surfaces having a smaller pore diameter and heat fusion welding was performed on outer edges thereof at 220° C. Thereby, a chamber for transplantation of Comparative Example 2 was produced. Furthermore, the polysulfone porous membrane was folded into two by facing surfaces having a larger pore diameter and direct heat fusion welding was performed on outer edges thereof at 220° C. Thereby, a chamber for transplantation of Comparative Example 3 was produced.

Comparative Example 4

Two polysulfone porous membranes of Comparative Example 1 were laminated so that the surfaces having a smaller average pore diameter were faced with each other, and they were bonded. Thereby, a polysulfone porous membrane having a compact portion within the membrane was obtained.

The laminated polysulfone porous membrane was folded into two and direct heat fusion welding was performed on outer edges thereof at 220° C. Thereby, a chamber for transplantation of Comparative Example 4 was produced.

<Structure Analysis of Porous Membrane>

(Measurement of Average Pore Diameter)

Each porous membrane obtained was impregnated with methanol and frozen in liquid nitrogen. Sections for cross section observation were cut out from the frozen porous membrane with a microtome (EM UC6, manufactured by Leica), and subjected to SEM imaging (SU8030 type FE-SEM, manufactured by Hitachi High-Technologies Corporation). SEM imaging was performed at 3000 times. 19 parting lines for dividing the SEM photograph of the cross section of each porous membrane into 20 from the upper side in the thickness direction are drawn, holes (closed hole) crossing or in contact with each parting line are traced with a digitizer, and thereby an average pore diameter of 50 consecutive holes was obtained. However, in a case where 50 holes could not be measured with one field of view of the SEM image because holes are large, a plurality of fields of view were prepared to measure 50 holes. The obtained average pore diameter of each parting line was plotted in order from one surface to the other surface, and thereby distribution of the average pore diameter in the thickness direction of the membrane was obtained. Pore diameter distribution of porous membranes of Examples 1 and 3 and Comparative Examples 1 and 2 is shown in FIG. 1. A portion including a parting line having the smallest average pore diameter was used as a compact portion, and the average pore diameter of this portion was measured by a separate ASTM F316-80 method.

A thickness of the compact portion is a product of the number of parting lines having an average pore diameter which is in a range of 1.1 times the minimum average pore diameter, and one-twentieth of the thickness of the membrane.

(Measurement of Porosity)

Each porous membrane obtained was impregnated with methanol and frozen in liquid nitrogen. From the frozen porous membrane, sections for porosity measurement were cut out to be parallel to the surface of each porous membrane with a sliding microtome (HM450, manufactured by Thermo SCIENTIFIC Inc.). For each porous membrane, a portion at one-fifth of a thickness of the porous membrane from the surface A was cut out as sections. A mass of the cut out section was measured by an electronic balance. A bulk density of the section was calculated from the measured mass, membrane thickness, and area. A porosity was calculated by the following formula.

Porosity (%)=(1−bulk density/true density)×100

The true density represents the density of the material constituting the porous membrane having no pores. For example, a true density of 1.24 was used for a case of polysulfone, and a true density of 2.15 was used for a case of polytetrafluoroethylene.

<Evaluation of Chamber for Transplantation and Porous Membrane>

(Wastes Permeability)

Each liquid was prepared, the liquid being obtained by adjusting a polystyrene latex dispersion liquid (Polybead Polystyrene Microspheres, manufactured by Polysciences, Inc.), which is regarded as wastes, such that a solid content became 0.1 mass % and a particle diameter became 40% to 50% of the average pore diameter of the compact portion of each porous membrane. A permeability of the dispersion liquid (a liquid permeation time of each filtration) was measured in a case where the dispersion liquid was filtered three times at a differential pressure of 10 kPa (100 ml/cm$^2$) from the surface B of each porous membrane. Each porous membrane was evaluated according to the following criteria. Here, t represents (time required for the first filtration/time required for the third filtration).

$0.95 \leq t \leq 1$     A:

$0.9 < t \leq 0.95$     B:

$t \leq 0.9$     C:

(Angiogenesis)

Each produced chamber for transplantation was transplanted into an abdominal cavity of rat, the abdomen was opened after 4 weeks to remove the chamber, and then the blood vessels on the inner surface of the rat epidermis in contact with the chamber and on the inner surface of the rat epidermis adjacent to the chamber (a control site) were observed. Therefore, the number of respective blood vessels was counted by a visual observation. Regarding each chamber for transplantation, the degree of angiogenesis was evaluated according to the following criteria.

A: The number of blood vessels 1.5 times or more that of the control site could be observed.

B: The number of blood vessels was more than that of the control site, but it was less than 1.5 times.

C: No significant difference from the control site was observed.

(Insulin Permeability)

A hole having a diameter of 1.0 cm was made in the center of one wall surface of a container made from vinyl chloride which has a size of 2.0 cm in length, 1.0 cm in width, and 2.0 cm in height, and the periphery of the hole was covered with a silicone sheet (50°, thickness of 1 mm) made from Tigers polymer. A porous membrane cut into 1.5 cm×2.0 cm was placed so as to cover the silicone sheet. Other same container and a silicone sheet were prepared and fixed with a clip such that the holes were aligned.

4.0 mL of a medium (medium for pancreatic islet culture, Cosmobio, PNIM3) containing 0.1 unit of insulin (Wako Pure Chemical Industries, Ltd., Insulin Humane Recombinant, 097-06474) was put into one container (supply side). 4.0 mL of the same medium but not containing insulin was put into the other container (permeation side). The surface B of the porous membrane was used as the supply side. After 60 minutes, the media on the supply side and permeation side were collected. An amount of insulin was quantitatively determined with Insulin ELISA (80-INSRT-E01, manufactured by ALPCO), and evaluated according to the following criteria.

An insulin concentration on the permeation side was 95% or more compared to the supply side after 60 minutes: AA An insulin concentration on the permeation side was 70% or more and less than 95% compared to the supply side after 60 minutes: A An insulin concentration on the permeation side was 45% or more and less than 70% compared to the supply side after 60 minutes: B An insulin concentration on the permeation side was less than 45% compared to the supply side after 60 minutes: C (Cell Infiltration Inhibitory)

Inhibition of cell infiltration into the inside of the membrane in a living body was evaluated on the porous membrane produced above, as follows. Evaluation of cell infiltration inhibitory is an indicator of a function of blocking various cells.

A 2 cm square porous membrane was implanted subcutaneously at the back of an SD rat (Sprague-Dawley rat) and sutured. After breeding for 1 week, the same portion was excised. Sections histologically stained with hematoxylin/eosin (HE) were produced. An image of a cross section of the portion where the porous membrane was implanted was captured. Each porous membrane was evaluated according to the following criteria.

resistance test. Therefore, the existence of interfacial peeling of the porous membrane was observed. Each porous membrane was evaluated according to the following criteria.

A: No interfacial peeling was observed.

B: Interfacial peeling was observed.

The results of the structure analysis and the evaluation are shown in Table 1.

TABLE 1

| Porous membrane | | | Compact portion | | Surface A | | Surface B |
|---|---|---|---|---|---|---|---|
| | Thickness (µm) | Material | Average pore diameter (µm) | Thickness (µm) | Average pore diameter (µm) | Porosity | Average pore diameter (µm) |
| Example 1 | 45 | PSF | 0.02 | 4.5 | 0.15 | 65% | 0.1 |
| Example 2 | 45 | PSF | 0.2 | 6.7 | 1.2 | 66% | 0.5 |
| Example 3 | 50 | PSF | 0.45 | 7.5 | 2.7 | 67% | 0.9 |
| Example 4 | 50 | PSF | 0.6 | 7.5 | 3.3 | 70% | 1.0 |
| Example 5 | 80 | PSF | 0.8 | 8 | 5.2 | 72% | 1.3 |
| Example 6 | 80 | PSF | 0.8 | 8 | 10 | 75% | 1.5 |
| Example 7 | 100 | PSF | 1.2 | 10 | 15 | 75% | 2.0 |
| Example 8 | 100 | PSF | 1.6 | 10 | 18 | 76% | 2.2 |
| Example 9 | 50 | PTFE | 0.6 | 7.5 | 3.2 | 69% | 1.0 |
| Comparative Example 1 | 50 | PSF | 0.44 | 7.5 | 2.5 | 63% | 0.8 |
| Comparative Example 2 | 50 | PSF | Surface B | | 2.3 | 70% | 0.5 |
| Comparative Example 3 | 50 | PSF | Surface A | | 0.45 | 61% | 2.3 |
| Comparative Example 4 | 100 | PSF | 0.45 | — | 2.3 | 70% | 2.3 |

| | Ratio of pore diameter A/B | Evaluation | | | | |
|---|---|---|---|---|---|---|
| | | Permeability | Angiogenesis | Insulin permeability | Cell infiltration inhibitory | Interfacial peeling |
| Example 1 | 1.9 | B | B | B | A | A |
| Example 2 | 2.4 | B | A | B | A | A |
| Example 3 | 3 | A | A | A | A | A |
| Example 4 | 3.3 | A | A | A | A | A |
| Example 5 | 4 | A | A | A | A | A |
| Example 6 | 6.7 | A | A | A | A | A |
| Example 7 | 7.5 | A | A | A | A | A |
| Example 8 | 8.2 | A | A | A | B | A |
| Example 9 | 3 | A | A | A | A | A |
| Comparative Example 1 | 2.5 | B | C | B | A | A |
| Comparative Example 2 | 22 | C | A | B | A | A |
| Comparative Example 3 | 0.2 | B | C | B | B | A |
| Comparative Example 4 | 1 | B | A | C | A | B |

A: A cell-infiltration-inhibiting layer was observed.

B: A cell-infiltration-inhibiting layer was observed, but a section where cells were infiltrated was observed in some part.

C: No clear cell-infiltration-inhibiting layer was observed, and cells were infiltrated throughout.

(Peeling Test Between Layers)

A sample with a width of 20 mm and a length of 100 mm was cut out from each porous membrane, and repeated bending test was performed with the sample using a U-shape folding tester (DLDLMS-4U, manufactured by YUASA SYSTEM Co. Ltd., radius 3 mm, stroke 10 mm, 3 Hz, 10,000 times, 35° C., 80% RH) in accordance with JIS-05016 (1994) of flexible printed wiring board bending

What is claimed is:

1. A chamber for transplantation, comprising:
    a membrane for immunoisolation at at least part of a boundary between an inside and an outside of the chamber for transplantation,
    wherein the membrane for immunoisolation includes a porous membrane,
    the porous membrane contains a polymer,
    the porous membrane is formed from a single composition as a single layer and has a layered compact portion where a pore diameter is the smallest within the membrane, a pore diameter continuously increases in a thickness direction from a compact portion toward both one surface A and the other surface B of the porous membrane, a porosity in a vicinity of the surface A is 65% or more, an average pore diameter of the surface A is larger than an average pore diameter of the surface B, and the surface B is disposed on the inside of the chamber for transplantation.

2. The chamber for transplantation according to claim 1, wherein an average pore diameter of the compact portion is 0.02 μm to 1.5 μm.

3. The chamber for transplantation according to claim 1, wherein the average pore diameter of the surface A is 1.0 μm to 100 μm.

4. The chamber for transplantation according to claim 1, wherein the average pore diameter of the surface B is 0.1 μm to 10 μm.

5. The chamber for transplantation according to claim 1, wherein the average pore diameter of the surface A is three times or more the average pore diameter of the surface B.

6. The chamber for transplantation according to claim 1, wherein a thickness of the compact portion is 0.5 μm to 30 μm.

7. The chamber for transplantation according to claim 1, wherein a thickness of the porous membrane is 10 μm to 50 μm.

8. The chamber for transplantation according to claim 1, wherein the porous membrane contains polysulfone or polyethersulfone, and at least one kind of hydrophilic polymers.

9. A device for transplantation, comprising the chamber for transplantation according to claim 1 enclosing a biological constituent therein.

10. The device for transplantation according to claim 9, wherein the biological constituent releases a physiologically active substance.

11. The device for transplantation according to claim 10, wherein the physiologically active substance is insulin.

12. A method for transplanting a biological constituent into a recipient, comprising enclosing a biological constituent in the chamber for transplantation according to claim 1.

13. The method according to claim 12, wherein the biological constituent releases a physiologically active substance.

14. The method according to claim 13, wherein the physiologically active substance is insulin.

15. The method according to claim 12, wherein the biological constituent is insulin-secreting cells.

16. A method for preventing an immune rejection by a recipient in a case of transplantation, comprising enclosing a biological constituent in the chamber for transplantation according to claim 1.

17. The method according to claim 16, wherein the biological constituent releases a physiologically active substance.

18. The method according to claim 17, wherein the physiologically active substance is insulin.

19. A method for manufacturing a chamber for transplantation, using a membrane for immunoisolation, wherein the membrane for immunoisolation includes a porous membrane, the porous membrane contains a polymer, the porous membrane is formed from a single composition as a single layer and has a layered compact portion where a pore diameter is the smallest within the membrane, a pore diameter continuously increases in a thickness direction from the compact portion toward both one surface A and the other surface B of the porous membrane, a porosity in a vicinity of the surface A is 65% or more, an average pore diameter of the surface A is larger than an average pore diameter of the surface B.

20. The method according to claim 19, comprising providing the membrane for immunoisolation at at least part of a boundary between an inside and an outside of the chamber for transplantation, disposing the surface B on the inside of the chamber for transplantation.

* * * * *